United States Patent [19]

Nelson et al.

[11] 4,059,611
[45] Nov. 22, 1977

[54] OXIDATIVE PROCESS FOR THE PREPARATION OF 2-(5H-DIBENZO[a,d]CYCLOHEPTEN-5-ON-2-yl)ACETIC, PROPIONIC AND BUTYRIC ACID

[75] Inventors: Peter H. Nelson; Karl G. Untch, both of Los Altos, Calif.

[73] Assignee: Syntex (U.S.A.) Inc., Palo Alto, Calif.

[21] Appl. No.: 702,651

[22] Filed: July 6, 1976

Related U.S. Application Data

[62] Division of Ser. No. 611,050, Sept. 8, 1975, abandoned.

[51] Int. Cl.$^2$ .................. C07C 143/68; C07C 65/14; C07C 83/00

[52] U.S. Cl. .................... 260/456 P; 260/501.1; 260/501.11; 260/501.15; 260/520 D; 260/438.1; 260/253; 260/501.17

[58] Field of Search ............... 260/456, 456 P, 520, 260/456 R, 520 D, 256 R, 501.1, 501.11, 501.15, 501.17, 438.1

[56] References Cited

U.S. PATENT DOCUMENTS

| | | | |
|---|---|---|---|
| 3,637,854 | 1/1972 | Kyburz et al. | 260/456 P |
| 3,933,905 | 1/1976 | Brunet et al. | 260/520 R |

*Primary Examiner*—James O. Thomas, Jr.
*Assistant Examiner*—W. B. Lone
*Attorney, Agent, or Firm*—Alan M. Krubiner

[57] ABSTRACT

2-(5H-Dibenzo[a,d]cyclohepten-5-on-2-yl) acetic, propionic and butyric acid, and esters and salts thereof, are prepared by oxidation of non-ketonic intermediates.

3 Claims, No Drawings

OXIDATIVE PROCESS FOR THE PREPARATION OF 2-(5H-DIBENZO[a,d]CYCLOHEPTEN-5-ON-2-yl)ACETIC, PROPIONIC AND BUTYRIC ACID

This is a division of application Ser. No. 611,050 filed Sept. 8, 1975, now abandoned.

DETAILED DESCRIPTION OF THE INVENTION

The present invention is concerned with a process for the preparation of 2-(5H-dibenzo[a,d]cyclohepten-5-on-2-yl) acetic, propionic and butyric acids, and esters and salts thereof. More specifically, the present invention concerns processes for the preparation of compounds of the formula

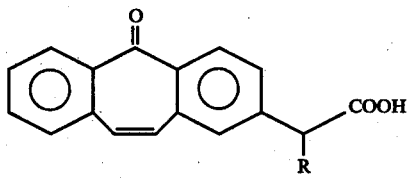

wherein R is hydrogen, methyl of ethyl, and the esters and salts thereof, from non-ketonic intermediates, by means of oxidative processes.

The compounds of Formula I exhibit anti-inflammatory, analgesic and anti-pyretic activity. Accordingly, compounds of Formula I and compositions containing same are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the compounds of Formula I are useful for the relief of these conditions as well as the inflammation.

The compounds of Formula I are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus.

As used herein, "esters" of the carboxylic acids of Formula I or intermediates therefor refer to those esters formed from straight or branched chain alkanols having from 1 to 20 carbon atoms, such as for example, the methyl, ethyl, n-propyl, isopropyl, n-butyl, t-butyl, n-amyl, n-hexyl, octyl, decyl, dodecyl, hexadecyl and octadecyl esters; as well as the benzyl esters. A preferred subclass of esters of Formula I are those formed from pharmaceutically acceptable non-toxic alcohols.

"Salts" of the carboxylic acids of Formula I or intermediates therefor refer to those salts prepared from inorganic and organic bases. Salts derived from inorganic bases include the alkali metal salts such as sodium, potassium and lithium; the alkaline earth salts such as calcium and magnesium; as well as the ammonium and copper salts. Those salts derived from organic bases include the ethanolamine, diethylamine, tris(hydroxymethyl)aminomethane, choline, caffeine, and lysine salts. A preferred subclass of salts of Formula I are those formed from pharmaceutically acceptable non-toxic bases.

The process of the present invention may be summarized in the reaction schemes presented below:

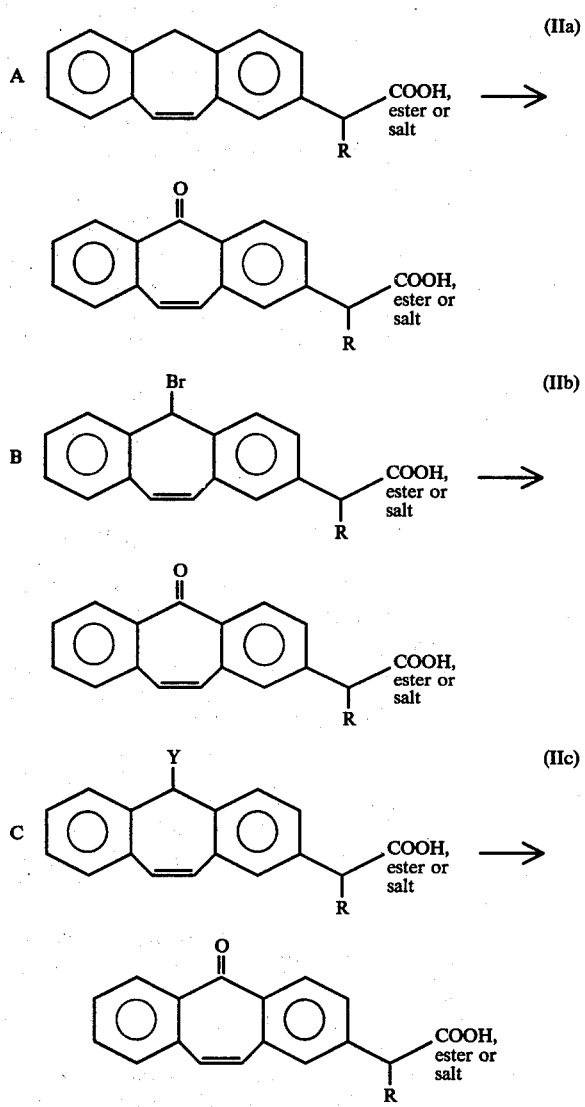

wherein R is as defined above and Y is hydroxy, alkylsulfonyloxy or arylsulfonyloxy.

In reaction scheme A is depicted the oxidation of a 5-unsubstituted acid, ester or salt of Formula (IIa) to the corresponding 5-oxo compound of Formula (I). Oxidative reactions of this type are well known in the art.

For example, such oxidation may be carried out utilizing ceric ammonium nitrate in an acidic medium. Such reaction is preferably carried out utilizing at least one molar equivalent of ceric ammonium nitrate. A preferred acidic medium for carrying out such reaction is aqueous acetic acid. This oxidation may be carried out over a wide temperature range, for example, from about 0° to about 110° C., most preferably about ambient temperature.

An alternative method for oxidizing a 5-unsubstituted compound of Formula (IIa) to the 5-oxo compound of Formula (I) is by treatment with oxygen in the presence of a base. This reaction may be carried out in a suitable organic solvent such as for example pyridine, dimethylsulfoxide, hexamethylphosphorictriamide, and the like.

As suitable bases there may be mentioned, for example, potassium t-butoxide, sodium methoxide and Triton B. For this reaction, oxygen is passed into a solution of the starting material and base for a sufficient period of time to effect the conversion. When starting with an ester or salt of Formulae (IIa), (IIb) or (IIc) only a small amount of base, for example, 0.1 equivalent, need be used, whereas when a free acid is utilized as starting material it is preferred to utilize an additional equivalent of base to first convert the acid to its salt.

In reaction scheme B is depicted the conversion of a 5-bromo compound of Formula (IIb) to the 5-oxo compound of Formula (I). This reaction may be carried out by heating the bromo compound of Formula (II) in dimethylsulfoxide. The reaction temperature necessary to effect this conversion is in the range of approximately 120° to 180° C., most preferably between about 150° and 170° C.

In reaction scheme C is depicted the conversion of a 5-hydroxy compound, or sulfonate ester thereof, of Formula (IIc) to the 5-oxo compound of Formula (I).

Oxidation of a 5-hydroxy compound to the corresponding 5-oxo compound may be accomplished by means well known in the art. For example, this oxidation may be accomplished by the use of well known reagents for the oxidation of hydroxy groups to ketones such as, for example, chromic (VI) reagents e.g., Jones reagent (chromic acid/sulfuric acid in acetone), chromic trioxide/pyridine and t-butyl chromate; alkali metal permanganates; activated manganese dioxide; and the like. These oxidations may be carried out in suitable inert solvents such as for example acetone, pyridine, acetonitrile, acetic acid, methylene chloride and mixtures of the above with water.

The oxidations may be carried out over a wide range of temperatures, for example, from about 0° to about 100° C., depending upon the choice of reagents and solvents.

In one preferred embodiment, the oxidation is carried out by means of activated manganese dioxide in acetonitrile at ambient temperature.

Sulfonate esters of Formula (IIc) may also be oxidized to the corresponding 5-oxo compounds of Formula (I). As sulfonate ester starting materials there may be mentioned alkylsulfonates such as, for example, methanesulfonates and arylsulfonates such as, for example, benzenesulfonates, p-toluenesulfonates, p-bromobenzenesulfonates, p-nitrobenzenesulfonates and naphthylsulfonates.

Oxidation of the sulfonate esters to the 5-oxo compound is carried out similarly to that for the oxidation of the 5-bromo compound, described supra, i.e., by heating in dimethylsulfoxide. However, the reaction with the sulfonate ester occurs, in general, much more rapidly than with the bromo compound so that heating at lower temperatures, for example from 80° to about 140° C., preferably about 120° C., in dimethylsulfoxide for shorter periods of time, is sufficient.

In the above reaction schemes A-C the starting materials and reagents may be contacted in any convenient manner and maintained at a temperature and for a period of time sufficient to complete the desired reaction. Furthermore, the reaction products may be isolated and recovered from the reaction using, as in the case of the reaction conditions themselves, procedures conventionally used in the art for conducting such reactions or analogous reactions.

The starting materials for reaction schemes A-C above may be prepared as follows:

The 5-unsubstituted acetic and propionic acids of Formula (IIa) are described in United States Patent 3,598,867. The corresponding butyric acid may be prepared, for example, by esterifying the acetic acid and reacting it with a base such as lithium diisopropylamide followed by alkylation with ethyl iodide and saponification.

The 5-bromo compounds of Formula (IIb) may be prepared by bromination of the corresponding 5-unsubstituted compounds of Formula (IIa) with, for example, N-bromosuccinimide in carbon tetrachloride.

The 5-alcohols of Formula (IIc) may be prepared from the corresponding bromides by, for example, hydrolysis with an alkali metal carbonate such as sodium carbonate in an aqueous solvent system such as aqueous tetrahydrofuran.

The 5-sulfonate esters of Formula (IIc) may be prepared by treating the 5-bromo compounds of Formula (IIb) with, for example, silver p-toluenesulfonate in acetonitrile.

Esters of the free acids of Formula (IIa), (IIb) and (IIc) may be prepared by conventional means, either by reaction of the corresponding acid chloride with a suitable alcohol or by esterification of the free acid with a diazoalkane such as diazomethane.

Salts of the carboxylic acids of Formulas (IIa), (IIb) and (IIc) may be prepared in the conventional manner by reacting the free carboxylic acid with the desired base.

The following examples illustrate preferred embodiments of the processes of the present invention. They should not be construed as limiting the scope or spirit of the invention in any manner. The yields of product obtained from the present process vary, depending upon the choice of starting material, reagents, reaction conditions, and workup. Generally, however the yields are in the range of from 10 to about 60 percent.

PREPARATION 1

A solution of 0.60 gm. of 2-(5H-dibenzo[a,d]cyclohepten-2-yl)propionic acid (reference: U.S. Pat. No. 3,598,867, compound named as 2-(2-dibenzo[a,d]cycloheptatrienyl)propionic acid) and 0.44 gm. of N-bromosuccinimide in 150 ml. of carbon tetrachloride is refluxed and irradiated with a 100 watt incandescent lamp for 1 hour. the solution is cooled, filtered and evaporated to afford 2-(5-bromo-5H-dibenzo[a,d]cyclohepten-2-yl)propionic acid.

Use of 2-(5H-dibenzo[a,d]cyclohepten-2-yl)acetic acid (alternate nomenclature 2-dibenzo[a,d]cycloheptatrienylacetic acid) affords 2-(5-bromo-5H-dibenzo[a,d]cyclohepten-2-yl)acetic acid.

PREPARATION 2

0.5 Gm. of 2-(5-bromo-5H-dibenzo[a,d]cyclohepten-2-yl)propionic acid is refluxed for 3 hours in 10 ml. of tetrahydrofuran and 25 ml. of water containing 0.5 gm. of sodium carbonate. The solution is cooled and washed with ether. The aqueous solution is then acidified with 0.5 N hydrochloric acid and extracted with ethyl acetate. The extract is washed, dried and evaporated to afford a 40% yield of 2-(5-hydroxy-5H-dibenzo[a,d]cyclohepten-2-yl)propionic acid.

Use of 2-(5-bromo-5H-dibenzo[a,d]cyclohepten-2-yl)acetic acid gives a similar yeild of 2-(5-hydroxy-5H-dibenzo[a,d]cyclohepten-2-yl)acetic acid.

EXAMPLE 1

1.10 Gm. of 2-(5H-dibenzo[a,d]cyclohepten-2-yl)propionic acid is refluxed for 2 hours in 10 ml. of acetic acid and 7.5 ml. of water containing 2.24 gm. of ceric ammonium nitrate. The solution is poured into water and extracted with ethyl acetate. The extract is washed, dried and evaporated and the residue chromatographed on silica gel, eluting with 40:60:1 ethyl acetate:hexane:acetic acid, so as to isolate a 30% yield of 2-(5H-dibenzo[a,d]cyclohepten-5-on-2-yl)propionic acid, m.p. (chloroform-hexane) 138°-139° C.; m.p. (acetone-hexane) 113°-115° C.

Use of 2-(5H-dibenzo[a,d]cyclohepten-2-yl)acetic acid gives a similar yield of 2-(5H-dibenzo[a,d]cyclohepten-5-on-2-yl)acetic acid, m.p. (acetone-hexane) 148°-149.5° C.

EXAMPLE 2

A. 1.0 Gm. of silver p-toluenesulfonate and 0.5 gm. of 2-(5-bromo-5H-dibenzo[a,d]cyclohepten-2-yl)propionic acid are stirred in 50 ml. of acetonitrile in the dark for 6 hours. Water, ether and 2.0 ml. of acetic acid are added. The ethereal layer is washed, dried and evaporated. The products, 2-(5-p-toluene-sulfonyloxy-5H-dibenzo[a,d]cyclohepten-2-yl)propionic acid, is dissolved in 10 ml. of dimethylsulfoxide and heated to 120° C. for 5 minutes, then cooled, poured into water and extracted with ethyl acetate. The solution is washed, dried and evaporated. The residue is chromatographed on silica gel, eluting with 40:60:1 ethyl acetate: acetic acid, so as to isolate a 15% yield of 2-(5H-dibenzo[a,d]cyclohepten-5-on-2-yl propionic acid, m.p. (chloroform-hexane) 138°-139° C.; m.p. (acetone-hexane) 113°-115° C.

Use of 2-(5-bromo-5H-dibenzo[a,d]cyclohepten-2-yl)acetic acid gives a similar yield of 2-(5H-dibenzo[a,d]cyclohepten-5-on-2-yl)acetic acid, m.p. (acetone-hexane) 148°-149.5° C.

B. 0.5 G. of 2-(5-bromo-5H-dibenzo[a,d]cyclohepten-2-yl)propionic acid is dissolved in 10 ml. of dimethylsulfoxide and heated at 150°-180° C. under nitrogen for 2 hours, then cooled, poured into water and worked up as in part A to afford 2-(5H-dibenzo[a,d]cyclohepten-5-on-2-yl)propionic acid.

EXAMPLE 3

0.25 Gm. of 2-(5-hydroxy-5H-dibenzo[a,d]cyclohepten-2-yl)propionic acid is stirred in 20 ml. of acetonitrile containing 2.0 gm. of activated manganese dioxide for 12 hours. The solution is then filtered and the filtrate evaporated to afford a 50% yield of 2-(5H-dibenzo[a,d]cyclohepten-5-on-2-yl)propionic acid, m.p. (chloroform-hexane) 138°-139° C.; m.p. (acetone-hexane) 113°-115° C.

Use of 2-(5-hydroxy-5H-dibenzo[a,d ]cyclohepten-2-yl)acetic acid gives a similar yield of 2-(5H-dibenzo[a,d]cyclohepten-5-on-2-yl)acetic acid, m.p. (acetone-hexane) 148°-149.5° C.

What is claimed is:

1. A compound represented by the formula

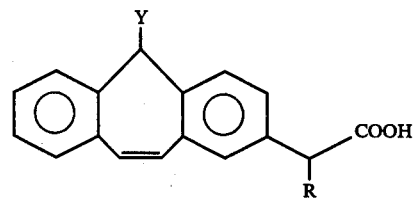

wherein R is hydrogen, methyl or ethyl and Y is hydroxy or a sulfonate moiety selected from the group consisting of methanesulfonyloxy, benzenesulfonyloxy, p-toluenesulfonyloxy, p-bromobenzenesulfonyloxy, p-nitrobenzenesulfonyloxy and naphthylsulfonyloxy; the esters thereof formed from straight or branched chain alkanols having from 1 to 20 carbon atoms or from benzyl alcohol; and the salts thereof selected from the group consisting of sodium, potassium, lithium, calcium, magnesium, ammonium, copper, ethanolamine, diethylamine, tris(hydroxymethyl)aminomethane, choline, caffeine and lysine salts.

2. A compound of claim 1 which is 2-(5-hydroxy-5H-dibenzo[a,d]cyclohepten-2-yl)propionic acid.

3. A compound of claim 1 which is 2-(5-p-toluenesulfonyloxy-5H-dibenzo[a,d]cyclohepten-2-yl)propionic acid.

* * * * *